(12) United States Patent
Dycus et al.

(10) Patent No.: US 10,004,526 B2
(45) Date of Patent: Jun. 26, 2018

(54) ULTRASONIC DISSECTION SYSTEM

(75) Inventors: Sean T. Dycus, Zurich (CH); Melissa J. Muszala, Wallisellen (CH)

(73) Assignee: COVIDIEN LP, Mansfield, MA (US)

( * ) Notice: Subject to any disclaimer, the term of this patent is extended or adjusted under 35 U.S.C. 154(b) by 482 days.

(21) Appl. No.: 13/189,670

(22) Filed: Jul. 25, 2011

(65) Prior Publication Data

US 2013/0030328 A1    Jan. 31, 2013

(51) Int. Cl.
| | |
|---|---|
| A61H 1/00 | (2006.01) |
| A61B 17/32 | (2006.01) |
| A61B 17/00 | (2006.01) |
| A61B 90/00 | (2016.01) |

(52) U.S. Cl.
CPC .......... *A61B 17/320092* (2013.01); *A61B 2017/00026* (2013.01); *A61B 2017/00084* (2013.01); *A61B 2017/00115* (2013.01); *A61B 2017/00119* (2013.01); *A61B 2090/064* (2016.02); *A61B 2090/0807* (2016.02)

(58) Field of Classification Search
CPC .............................. A61N 7/00; A61H 23/0245
USPC ............................................................ 601/2
See application file for complete search history.

(56) References Cited

U.S. PATENT DOCUMENTS

| | | | | |
|---|---|---|---|---|
| 6,331,172 B1* | 12/2001 | Epstein | ............ | A61B 17/00491 604/191 |
| 6,790,187 B2 | 9/2004 | Thompson et al. | | |
| 6,839,579 B1* | 1/2005 | Chin | .................... | A61B 5/1491 600/323 |
| 7,476,233 B1 | 1/2009 | Wiener et al. | | |
| 2002/0111624 A1* | 8/2002 | Witt et al. | ........................ | 606/51 |
| 2003/0018295 A1* | 1/2003 | Henley et al. | ................... | 604/20 |
| 2003/0139742 A1* | 7/2003 | Wampler et al. | ................ | 606/51 |
| 2005/0203504 A1* | 9/2005 | Wham et al. | .................... | 606/34 |
| 2007/0173814 A1* | 7/2007 | Hixson et al. | .................. | 606/51 |
| 2009/0318804 A1 | 12/2009 | Avital et al. | | |
| 2010/0010352 A1 | 1/2010 | Jong | | |
| 2010/0204643 A1 | 8/2010 | Sarvazyan | | |
| 2011/0004513 A1 | 1/2011 | Hoffberg | | |
| 2011/0241786 A1 | 10/2011 | Gilbert | | |

FOREIGN PATENT DOCUMENTS

JP    2000237204    9/2000

OTHER PUBLICATIONS

U.S. Appl. No. 13/108,117, filed May 16, 2011, Andrey Balanev.
U.S. Appl. No. 13/149,570, filed May 31, 2011, William N. Gregg.
U.S. Appl. No. 13/189,670, filed Jul. 25, 2011, Sean T. Dycus.

* cited by examiner

*Primary Examiner* — Hien Nguyen

(57) ABSTRACT

An ultrasonic surgical system is provided. The ultrasonic surgical system includes an ultrasonic instrument that is configured to ultrasonically treat tissue. An ultrasonic generator configured to provide ultrasonic energy to the ultrasonic instrument provides an indication to a user that a specific outcome has been achieved. The indication is output via a device selected from an audio activation end-tone device, a visual activation end-tone device or a tactile activation end-tone device. The ultrasonic generator includes an end-tone outcome indicator module that includes memory having one or more data look up tables that is accessible by a microprocessor associated with the ultrasonic generator.

4 Claims, 4 Drawing Sheets

US 10,004,526 B2

ULTRASONIC DISSECTION SYSTEM

BACKGROUND

Technical Field

The present disclosure relates to systems and methods for providing energy to tissue and, more particularly, to an ultrasonic dissection system including an ultrasonic generator configured to provide activation end points for ultrasonic dissection.

Background of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy may be delivered to tissue using a surgical probe that includes a transducer coupled to an end effector configured to deliver ultrasonic energy to tissue.

The use of ultrasonic energy in surgical procedures is known to those skilled in the art to be a valuable resource for cutting and fragmenting tissue of a patient. Most of these apparatus incorporate a sinusoidal driving signal which causes the mechanical tip to vibrate at a selected frequency, usually in the range of 20 KHz to 60 KHz.

Currently, surgeons use visual feedback, such as steam, thermal tissue spread, and experience to decide how and when apply to ultrasonic energy to tissue

SUMMARY

The present disclosure provides an ultrasonic surgical system. The ultrasonic surgical system includes an ultrasonic instrument that is configured to ultrasonically treat tissue. An ultrasonic generator configured to provide ultrasonic energy to the ultrasonic instrument provides an indication to a user that a specific outcome to tissue has been achieved. The indication is output via a device selected from an audio activation end-tone device, a visual activation end-tone device or a tactile activation end-tone device. The ultrasonic generator includes an end-tone outcome indicator module that includes memory having one or more data look up tables that is accessible by a microprocessor associated with the ultrasonic generator.

The present disclosure provides an ultrasonic surgical system. The ultrasonic surgical system includes an ultrasonic instrument including at least one end-tone indication device operably disposed thereon. An ultrasonic generator in operable communication with the ultrasonic instrument is configured to provide ultrasonic energy thereto. The ultrasonic generator includes an end-tone outcome indicator module operable to control the at least one end-tone indication device to provide an indication to a user that a specific outcome relating to tissue has been achieved.

The present disclosure provides a method for performing an ultrasonic procedure. The method includes grasping tissue with an ultrasonic instrument. Thereafter, ultrasonic energy is delivered via an ultrasonic generator to the ultrasonic instrument. A first indication is provided to the user indicating that a first outcome has been achieved. A second indication is provided to the user indicating that a second outcome has been achieved.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
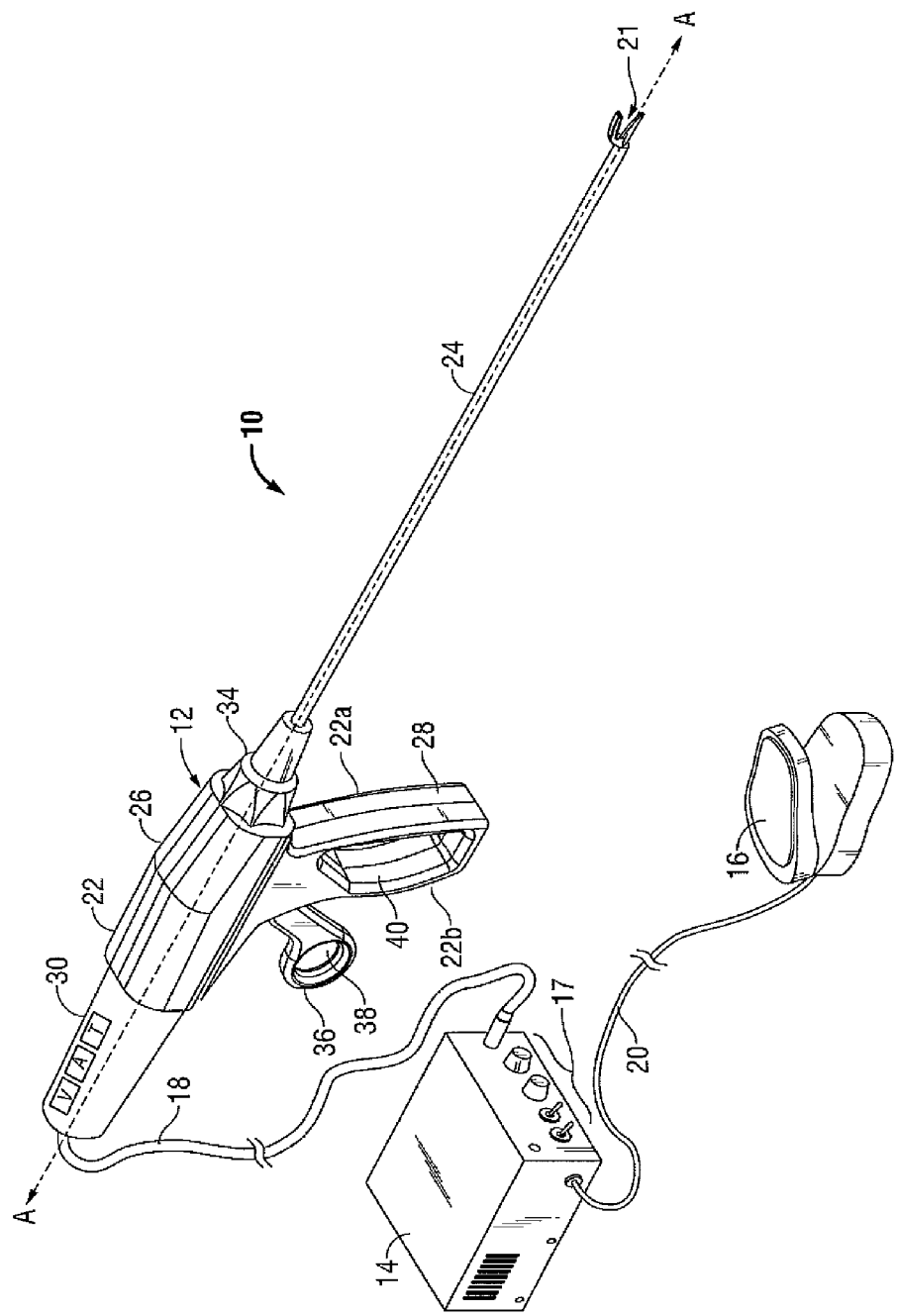
FIG. 1 is a perspective view of an ultrasonic dissection system including an ultrasonic dissection instrument configured for use with an ultrasonic generator in accordance with the present disclosure.

Particular embodiments of the present disclosure are described hereinbelow with reference to the accompanying drawings, however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

FIG. 1 illustrates an ultrasonic dissection and coagulation system 10 that includes an ultrasonic instrument 12, an ultrasonic generator module 14, and a remote actuator 16. Briefly, ultrasonic generator module 14 (generator module 14) is operatively connected to ultrasonic instrument 12 by an electrically conductive cable 18 and functions to control the power and frequency of current supplied to ultrasonic instrument 12. Actuator 16, e.g., a foot switch, is operatively connected to ultrasonic generator module 14 by cable 20. Actuator 16 may be actuated to activate generator module 14, which, in turn, causes an ultrasonic driving signal to be delivered to a transducer 30 of ultrasonic instrument 12. Generator module 14 includes a user interface module 17. Transducer 30 is operably coupled with ultrasonic end effector 21 of instrument 12 by way of a vibration coupler (contained within band portion 26 and body portion 24 extending from a housing 22). Transducer 30 converts an ultrasonic driving signal received from generator module 14 into ultrasonic energy (e.g., acoustic or mechanical wave energy), which, in turn, is delivered to end effector 21 to cut and/or coagulate tissue. Ultrasonic transducer 30 is supported within and extends from the proximal end of housing 22 and is coupled to ultrasonic generator module 14 via cable 18. Housing 22 may be formed from molded housing half-sections 22a and 22b and includes barrel portion 26 having a longitudinal axis aligned with the longitudinal axis of body portion 24, and a stationary handle portion 28 extending obliquely from barrel portion 26. The ultrasonic end effector 21 is disposed adjacent the distal end of elongated body portion 24 and is actuated by moving movable handle 36 with respect to stationary handle portion 28. Movable handle 36 and stationary handle portion 28 may include openings (apertures, holes, grooves, slots, etc.) 38 and 40, respectively, defined therein that facilitate gripping and actuation of ultrasonic instrument 12. Elongated body portion 24 is supported within rotatable knob 34 and may be selectively rotated by rotating knob 34 with respect to housing 22 to change the orientation of the distal end of ultrasonic instrument 12. For a more detailed description of the ultrasonic instrument 12, reference is made to commonly-owned co-pending U.S. patent application Ser. No. 12/713,266 to Mathonnet, filed Feb. 26, 2010.

Figure 2:
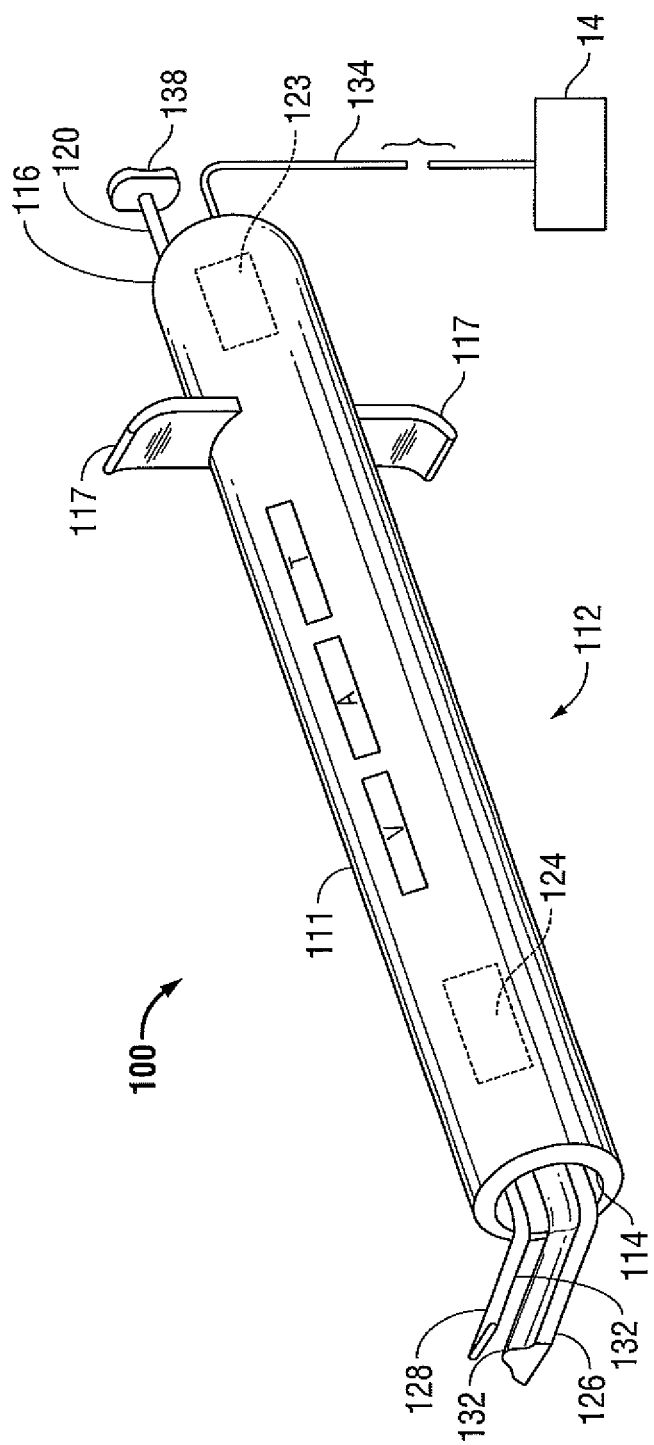
FIG. 2 is a perspective view of an ultrasonic dissection system including another embodiment of an ultrasonic dissection instrument configured for use with the ultrasonic generator.

FIG. 2 illustrates an ultrasonic dissection and coagulation system 100 that includes an ultrasonic instrument 112 and an ultrasonic generator module 14. Briefly, ultrasonic instrument 112 includes a substantially cylindrical outer housing 111 having an open distal end 114 and a closed proximal end 116. The housing 111 may be formed with a gripping member 117. The proximal end 116 of housing 111 is formed with a slot (not explicitly shown) dimensioned to slidably receive an actuation rod 120. In this embodiment, generator module 14 is electrically connected to a transducer 123 via conventional means, such as a power cable 134. The transducer 123 is supported within the housing 111 and engages a vibrator coupler 124 that extends longitudinally towards the distal end 114 of housing 111. A blade member 126 having a cutting edge 132 is provided at the distal end 114 of the vibration coupler 124. The blade member 126 is fixedly connected to the vibration coupler 124 or alternately integral therewith, such that the cutting edge 132 defines a plane oriented at an acute fixed angle, preferably from about 30 degrees to about 70 degrees, with respect to the longitudinal axis of the instrument. For a more detailed description of the ultrasonic instrument 112, reference is made to commonly-owned co-pending U.S. Pat. No. 6,869,439 to White et al., filed Aug. 19, 2002.

For illustrative purposes, the generator module 14 is described in terms of use with the ultrasonic instrument 12.

Figure 3:
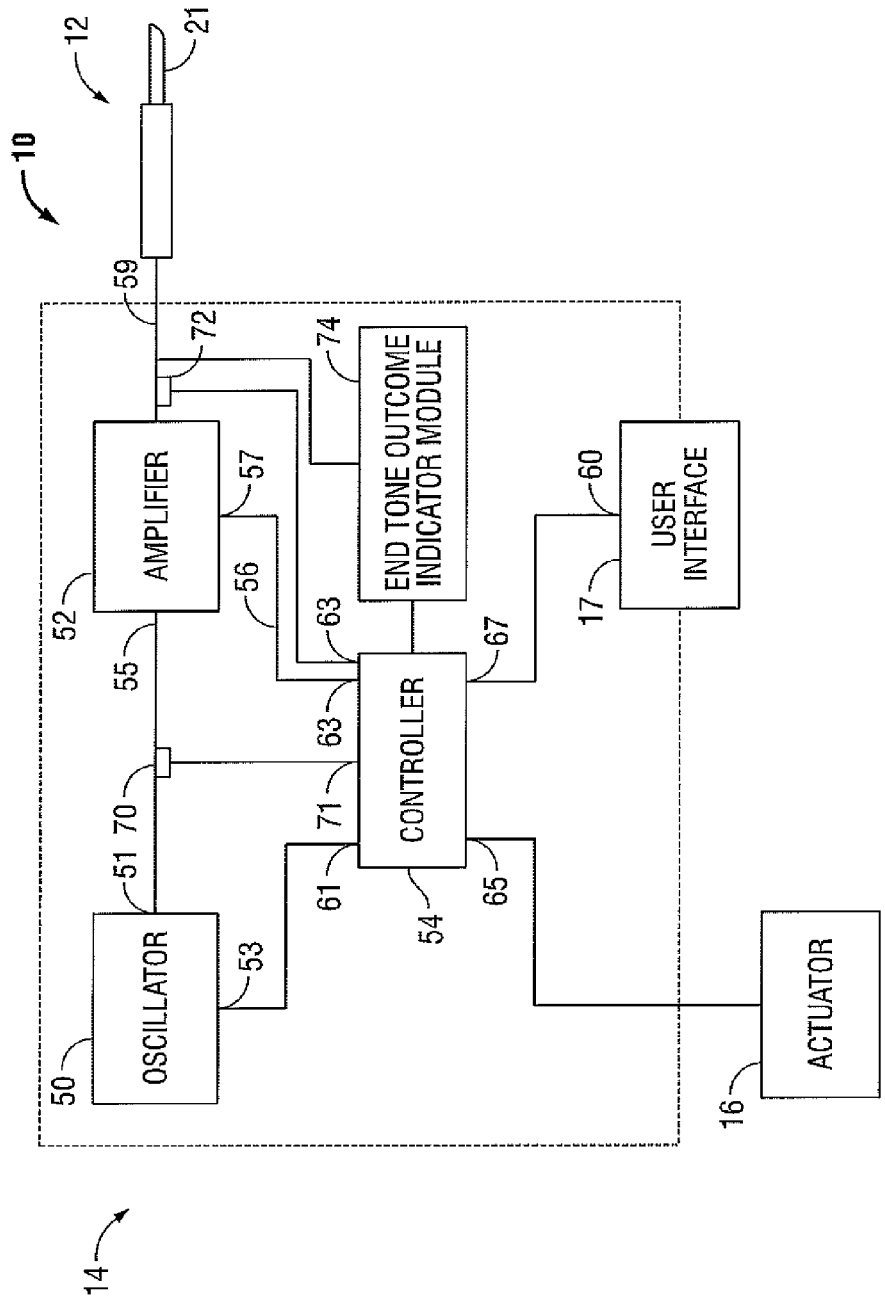
FIG. 3 is a block diagram of the ultrasonic dissection system depicted in FIG. 1.

FIG. 3 illustrates a functional block diagram of the ultrasonic dissection system 10 including the operative components of the generator module 14. Generator module 14 supplies an alternating current electrical signal having an ultrasonic frequency to the transducer 30 to cause oscillation thereof. With this purpose in mind, generator module 14 includes an amplifier 52 that receives a signal input 55 and produces a driving signal output 59, and an amplifier control input 57. Amplifier 52 is configured to respond to an amplifier control signal 56 received at control input 57 from an amplifier control signal output 63 of controller 54 to adjust an amplifier operating parameter, including without limitation, gain, attenuation, phase, output voltage, output current, output power, etc. Driving signal output 59 is operatively coupled with ultrasonic instrument 12 to provide an ultrasonic driving signal thereto.

Controller 54 is in operable communication with an oscillator 50, amplifier 52, actuator 16, and user interface module 17. The communication may be continuous or intermittent. Controller 54 is programmed to process data to control the generation of the ultrasonic energy, as described herein. Controller 54 may be embodied in any of hardware, software, software in execution, firmware, microcode, bytecode, in virtualization, in a hardware description language, logic gates, circuitry, digital circuitry, RAM, ROM, MEMS, and the like.

Controller 54 is further configured to receive one or more actuator inputs 65 from the actuator 16 to selectively control the generation of a desired ultrasonic drive signal. In embodiments, ultrasonic dissection and coagulation system 10 may include two or more actuators 16 that may be coupled to corresponding actuator inputs 65 of controller 54 to enable a user, e.g., a surgeon, to selectively activate ultrasonic dissection and coagulation system 10 in one or more predetermined operating modes.

Controller 54 may include a microprocessor (not explicitly shown) that is operably connected to a memory (not explicitly shown) which may be volatile type memory (e.g., RAM) and/or non-volatile type memory (e.g., flash media, disk media, etc.). Controller 54 may include any suitable logic processor (e.g., control circuit), hardware, software, firmware, or any other logic control adapted to perform the features discussed herein.

User interface module 17 is configured to receive user input, and provide at least one user interface signal to controller 54. Controller 54 interprets the user input and controls the operation of ultrasonic dissection and coagulation system 10 in accordance therewith. More particularly, controller 54 is configured to control oscillator 50 and amplifier 52 to generate at least one ultrasonic dissection and/or coagulation waveform as described herein. In particular, oscillator 50 generates waveforms in a range of about 20 KHz to about 60 KHz, which may be processed by amplifier 53 to generate one or more ultrasonic dissection and/or coagulation waveforms having various duty cycles, frequencies, peak voltages, peak currents, peak power, and other suitable characteristics.

The user interface module 17 may include one or more input controls, such as, without limitation, buttons, continuous controls, rotary and/or linear potentiometers, encoders, switches, touch screens, and the like, for controlling at least one operating parameter of ultrasonic dissection and coagulation system 10. Additionally or alternatively, user interface module 17 may include one or more visual and/or display screens (not explicitly shown) or audio indicators for providing the user with variety of output information (e.g., intensity settings, treatment complete indicators, end-tones, etc.). The user interface module 17 allows a user (e.g., a surgeon, nurse, or technician) to adjust the ultrasonic energy parameters (e.g., operating mode, output power, waveform, duty cycle, drive voltage, drive current, frequency, and/or other parameters) to achieve the desired ultrasonic energy characteristics suitable to achieve a surgical objective (e.g., dissection, coagulating or other tissue treatments). Additionally or alternatively, user interface module 17 may include a user-selectable desired tissue effect (e.g., hemostasis, coagulation, ablation, dissection and/or cutting).

In accordance with the present disclosure, the generator module 14 is configured to provide activation end-tones for the ultrasonic device 12 during the course of ultrasonic treatment of tissue, e.g., a vessel. For example, and in one particular embodiment, the end-tones may be provided by an audible indicator activation device "A" (e.g., audible tones), a visual indicator activation device "V" (e.g., LEDs, lights, etc.), or in some instances, a tactile indicator activation device "T" such as, for example, vibrations or the like, see FIGS. 1 and 2. Similar to that of a manual transmission of a car that is configured to indicate to an operator when to shift gears, e.g., shift to a next, higher gear, or, the lights at an airport that indicate to a pilot that the plane is on a correct glide slope, the end-tones provide an indication to an end user, e.g., a surgeon, that a specific occurrence or outcome has been or is being achieved. In particular, the end-tones function to provide indication that one or more specific occurrences or outcomes have been achieved during an ultrasonic surgical procedure, e.g., minimum burst of tissue at one times (1×) systolic blood pressure, low end of thermal spread, optimal dissection speed, correct application of pressure at the jaw members of the end effector 12, etc. With this purpose in mind, the controller 54 is in operable communication with an end-tone outcome indicator module 74 (EOIM 74) that communicates with the above-referenced indicators "A," "V" and "T". EOIM 74 may be configured to activate the indicators "A," "V" and "T" so that the indicators "A," "V" and "T" are operable at a specific frequency, power level or intensity, etc., to indicate to a surgeon that a specific outcome has been or is being reached.

In the illustrated embodiment, empirical data obtained through testing a significant population of vessel sizes is stored in memory, e.g., a data look-up table, of the EOIM 74 and is accessible by the microprocessor and/or controller 54. The empirical data may include such information as vessel size and various characteristics associated with the vessel at that specific size for a specific surgical procedure, e.g., rate of tissue coagulation, rate of dissection, rate of thermal spread, etc. The vessel data may be compiled or otherwise tabulated for specific vessel sizes, i.e., 5 mm, 6 mm, 7 mm, etc., or specific vessel ranges, i.e., 1-2 mm, 2-5 mm, 5-7 mm, etc. A graph of the compiled or tabulated data is stored into memory of the EOIM 74 and may be accessible by the microprocessor and/or controller 54.

Figure 4:
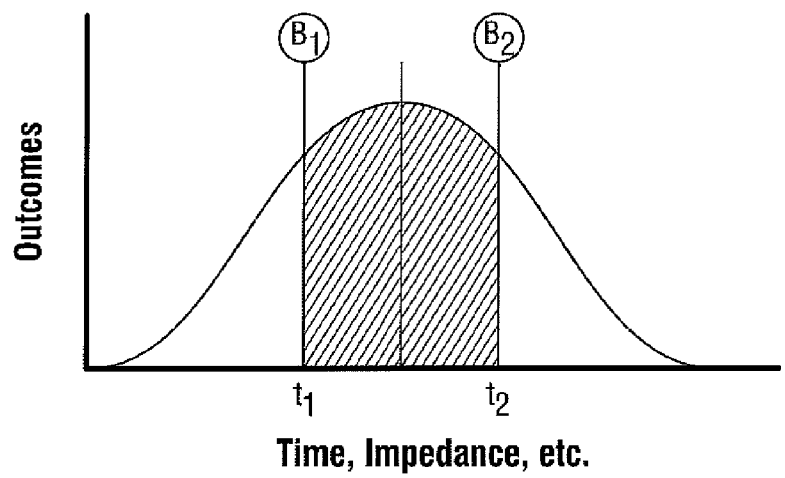
FIG. 4 is a graphical representation of a specific outcome as a function of one or more physical or electrical variables.

With reference to FIG. 4, the graph (or section thereof) may be utilized to give end-tones for specific outcomes as a function of time, temperature, impedance, etc. In one particular embodiment, the outcome may be a low end of thermal spread for a given vessel size, wherein application of ultrasonic energy is applied at a specific power or intensity and for a given time period. For instance, an end-tone, e.g., an audio end-tone provided by the audible indicator "A," may occur at ""B1" at time "t1" and indicate to a surgeon that the low end of thermal spread has been reached with a minimum burst of 1× systolic blood pressure. Moreover, an end-tone, e.g., an audio end-tone provided by the audible indicator "A," may occur at ""B2" at time "t2," which would indicate to a surgeon that a high end of thermal spread has occurred.

In one particular embodiment, the EOIM 74 may be configured to provide indication to a surgeon that the surgeon is applying a correct pressure or closure force (for a given intensity or power level) at the jaw members of the end effector during the ultrasonic surgical procedure. In this instance, the EOM 74 may communicate with the audible indicator "A," such that the audible indicator "A," provides a constant, or in some instances, a changing, tone when the surgeon is applying the correct pressure or closure force at the jaw members. In this specific surgical scenario, the above graph represents an outcome that is "optimal dissection speed" as a function of pressure or closure force at the jaw members.

Figure 5:
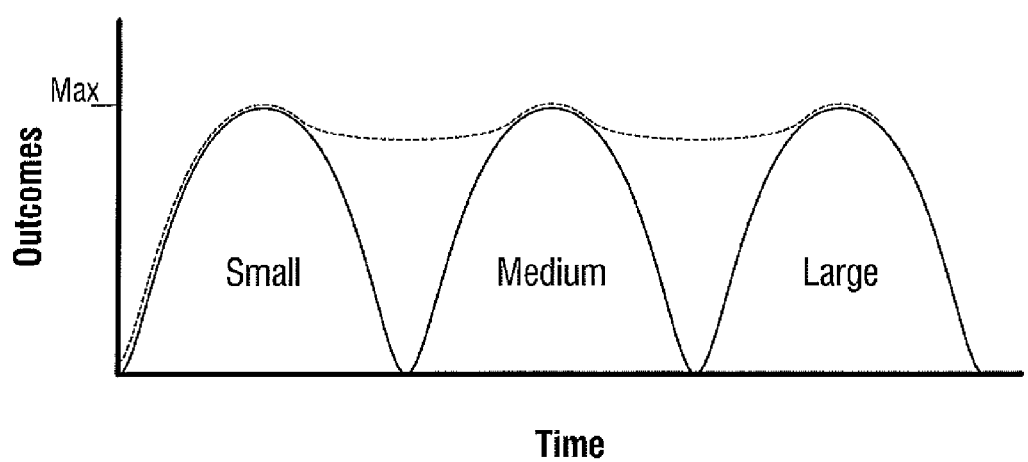
FIG. 5 is a graphical representation of a specific outcome as a function of time.

With reference to FIG. 5, a method to implement activation end-tones in accordance with the present disclosure is illustrated. In this instance, the graph (or section thereof) illustrates three (3) curves for small (1 mm to about 2 mm), medium (2 mm to about 5 mm) and large vessels (5 mm to about 7 mm). In FIG. 5, one of the previously described maximum outcomes as a function of time "t" is associated with each of the small, medium and large vessels. As one of the small, medium and large vessels is ultrasonically treated, based on empirical data, the end points or maximum outcomes are reached for each size vessel. Accordingly, the audible "A," visual "V" or tactile "T" indication changes as the maximum outcome is reached for each vessel size. Based on a surgeon's knowledge of the specific vessel that the surgeon is applying ultrasonic energy to, the surgeon may choose to stop at any point along the curve for each vessel size. For example, and in one particular embodiment, a surgeon positions a large vessel between the jaws of the end effector and applies ultrasonic energy thereto. The end-tone, e.g., audible end-tone provided by audible indicator "A," would rise to a maximum level (i.e., for the small vessel) and, subsequently, decrease to a minimum level. The end-tone, again provided by audible indicator "A," would again rise to a maximum level (i.e., for the medium vessel) and, subsequently, decrease to a minimum level. The end-tone, again provided by audible indicator "A," would again rise to a maximum level (i.e., for the large vessel), where, if desired, the surgeon could choose to stop the application of ultrasonic energy, i.e., the maximum outcome for that specific vessel has been reached.

In use, a surgeon grasps tissue via the ultrasonic instrument 12. Ultrasonic energy is supplied to the ultrasonic instrument 12 via the generator module 14. EOIM 74 tracks progression of the ultrasonic procedure. When a first outcome is reached, the EOIM 74 signals one or more of the activation end-tone devices, e.g., the audio end-tone device "A." In one particular embodiment, the activation end-tone device "A" generates a consistent audible tone to indicate to the surgeon that a first desired outcome, e.g., low end of thermal spread has been reached (FIG. 4). Depending on the vessel size, i.e., small, medium or large (FIG. 5), the surgeon may continue (or discontinue) to ultrasonically treat the vessel.

From the foregoing and with reference to the various figure drawings, those skilled in the art will appreciate that certain modifications can also be made to the present disclosure without departing from the scope of the same. For example, in certain instances, system 10 may include one or more sensors configured to sense a property of tissue as the tissue is being ultrasonically treated. For example, one or more sensors may be in operable communication with the EOIM 74 to provide feedback regarding one or more parameters of the vessel as the vessel is being ultrasonically treated. For example, and in one particular embodiment, a temperature sensor may be positioned on one or both of the jaw members of the end effector and may be configured to provide real-time temperature readings of tissue, e.g., a vessel. In this instance, the temperature sensor may communicate with the EOIM 74 to provide additional information thereto as a vessel is being ultrasonically being treated.

Moreover, the ultrasonic instrument 12 may be configured and employed to seal tissue. In this instance, one or more stop members may be utilized to control the gap between jaw members. In addition, one or more devices, e.g., resilient members or the like, may be utilized to provide and or control an appropriate pressure between the jaw members when the jaw members are in the clamping configuration. Further, one or more devices operably associated with the ultrasonic instrument 12 and/or generator module 14 may be configured to the control the amount of electrosurgical energy provided to the jaw members.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An ultrasonic surgical system, comprising:
an ultrasonic instrument configured to ultrasonically treat tissue, the ultrasonic instrument including at least one indicator operably disposed thereon;
an ultrasonic generator in communication with the ultrasonic instrument and configured to provide ultrasonic energy thereto; and
an outcome indicator module included within the ultrasonic generator and configured, for each of first, second, and third specific tissue-effect outcomes for respective first, second, and third tissue sizes of vessels ranging from 1 mm-2 mm, from 2 mm-5 mm, and from 5 mm-7 mm, respectively, to control the at least one indicator to provide: (1) a changing indication that the specific tissue-effect outcome for the tissue size is being achieved; and (2) a second indication that the specific tissue-effect outcome for the tissue size has been achieved, the outcome indicator module including at least one data look up table including empirical data including at least one predetermined time value that corresponds to a maximum value obtained for the specific tissue-effect outcome for the tissue size, wherein the outcome indicator module is programmed to track progression of the specific tissue-effect outcome for the tissue size along a graph of the empirical data and provide an indication for a duration that the progression of the specific tissue-effect outcome for the tissue size is being tracked along the graph of the empirical data,
the at least one indicator configured to receive the changing indication and the second indication from the outcome indicator module and provide an output to a user of the changing indication and the second indication, the output provided via the at least one indicator operably disposed on the ultrasonic instrument,
wherein the changing indication begins at a first indication and transitions to the second indication, and
wherein the specific tissue-effect outcome for the tissue size is burst pressure or thermal spread.

2. The ultrasonic surgical system according to claim 1, wherein the outcome indicator module includes a memory having at least one data look up table that is accessible by a microprocessor associated with the ultrasonic generator.

3. A method for performing a surgical procedure, comprising:
grasping tissue with an ultrasonic instrument;
delivering ultrasonic energy via an ultrasonic generator to the ultrasonic instrument;
tracking progression of a first specific tissue-effect outcome, a second specific tissue-effect outcome, and a third specific tissue-effect outcome along a graph of empirical data including first, second, and third predetermined times obtained for respective vessels ranging from 1 mm-2 mm, from 2 mm-5 mm, and from 5 mm-7 mm, the first, second, and third predetermined times corresponding to first, second, and third maximum values obtained for each of the first specific tissue-effect outcome, the second specific tissue-effect outcome, and the third specific tissue-effect outcome;
providing a changing indication of the first specific tissue-effect outcome indicating that the first specific tissue-effect outcome is being achieved, wherein the changing indication of the first specific tissue-effect outcome begins at a first indication of the first specific tissue-effect outcome and transitions to a second indication of the first specific tissue-effect outcome;
providing the second indication of the first specific tissue-effect outcome indicating that the first specific tissue-effect outcome has been achieved;
providing a second changing indication of the second specific tissue-effect outcome indicating that the second specific tissue-effect outcome is being achieved, wherein the second changing indication of the second specific tissue-effect outcome begins at a first indication of the second specific tissue-effect outcome and transitions to a second indication of the second specific tissue-effect outcome;
providing the second indication of the second specific tissue-effect outcome indicating that the second specific tissue-effect outcome has been achieved;
providing a third changing indication of the third specific tissue-effect outcome indicating that the third specific tissue-effect outcome is being achieved, wherein the third changing indication of the third specific tissue-effect outcome begins at a first indication of the third specific tissue-effect outcome and transitions to a second indication of the third specific tissue-effect outcome;
providing the second indication of the third specific tissue-effect outcome indicating that the third specific tissue-effect outcome has been achieved; and
outputting the changing indication of the first specific tissue-effect outcome, the second indication of the first specific tissue-effect outcome, the second changing indication of the second specific tissue-effect outcome, the second indication of the second specific tissue-effect outcome, the third changing indication of the third specific tissue-effect outcome, and the second indication of the third specific tissue-effect outcome,
wherein the outputting is provided via an indicator operably disposed on the ultrasonic instrument, and
wherein at least one of the first specific tissue-effect outcome, the second specific tissue-effect outcome, or the third specific tissue-effect outcome is burst pressure or thermal spread.

4. The method according to claim 3, wherein the ultrasonic generator includes an outcome indicator module including memory having at least one data look up table that is accessible by a microprocessor associated with the ultrasonic generator.

* * * * *